(12) United States Patent
Chopra et al.

(10) Patent No.: US 6,387,357 B1
(45) Date of Patent: May 14, 2002

(54) HIGH OIL CLEAR EMULSION WITH DIENE ELASTOMER

(75) Inventors: Suman Chopra, Dayton; Jairajh Mattai, Piscataway; Lin Fei, Scotch Plains; Eric Guenin, Pennington; Xiaozhong Tang, Bridgewater; Claudio Ortiz, Dayton, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/693,229

(22) Filed: Oct. 20, 2000

(51) Int. Cl.$^7$ .............. A61K 7/32; A61K 7/34; A61K 7/38; A61K 7/00
(52) U.S. Cl. .............. 424/65; 424/66; 424/68; 424/400; 424/401
(58) Field of Search .............. 424/65, 66, 68, 424/400, 401

(56) References Cited

U.S. PATENT DOCUMENTS

| | | |
|---|---|---|
| 3,979,510 A | 9/1976 | Rubino |
| 4,021,536 A | 5/1977 | Rubino |
| 4,673,570 A | 6/1987 | Soldati |
| 4,980,156 A | 12/1990 | Raleigh et al. |
| 5,008,103 A | 4/1991 | Raleigh et al. |
| 5,292,503 A | 3/1994 | Raleigh et al. |
| 5,401,870 A | 3/1995 | Raleigh et al. |
| 5,463,098 A | 10/1995 | Giovanniello et al. |
| 5,534,246 A | 7/1996 | Herb et al. |
| 5,587,153 A | 12/1996 | Angelone, Jr. et al. |
| 5,587,173 A | 12/1996 | Junino et al. |
| 5,599,533 A | 2/1997 | Stepniewski et al. |
| 5,623,017 A | 4/1997 | Hill |
| 5,922,308 A | 7/1999 | Brewster et al. |
| 5,925,338 A | 7/1999 | Karassik et al. |
| 5,955,065 A | 9/1999 | Thong et al. |
| 5,989,531 A | 11/1999 | Schamper et al. |
| 6,010,688 A | 1/2000 | Shen |
| 6,060,546 A | 5/2000 | Powell et al. |
| 6,103,250 A | 8/2000 | Brieva et al. |

FOREIGN PATENT DOCUMENTS

| | | |
|---|---|---|
| EP | 0787758 A1 | 4/1997 |
| WO | WO 92/19221 | 11/1992 |
| WO | WO 98/00105 | 6/1996 |
| WO | WO 97/44010 | 11/1997 |
| WO | WO 98/00097 | 1/1998 |
| WO | WO 98/00104 | 1/1998 |
| WO | WO 98/18438 | 5/1998 |
| WO | WO 98/42307 | 10/1998 |
| WO | WO 99/51192 | 10/1999 |

*Primary Examiner*—Shelley A. Dodson
(74) *Attorney, Agent, or Firm*—Rosemary M. Miano

(57) ABSTRACT

A clear antiperspirant and/or deodorant composition is disclosed in the form of an emulsion having a refractive index less than 1.42 and comprising: (a) 25–70% of an external phase comprising: (i) 0.1–10%, on an actives basis, of at least one elastomer which is a cyclomethicone (and) dimethicone crosspolymer made with an ≡Si—H containing polysiloxane and an alpha, omega-diene of formula $CH_2=CH(CH_2)_xCH=CH_2$, where x=1–20, to form a gel by crosslinking and addition of ≡Si—H across double bonds in the alpha, omega diene, which crosspolymer has a viscosity in the range of 50,000–3,000,000 centipoise; (ii) 0.1–5% of a silicone copolyol having an HLB value ≦8; (iii) 0.1–68% of a volatile silicone selected in an amount to complete the external phase; (iv) 0–10% of a cosurfactant or emulsifier having an HLB value in the range of 1–15; (v) 0–5% of a non-volatile silicone; and (b) 30–75% of an internal phase which is made with: (i) 7–25% (on an anhydrous actives basis (excluding the waters of hydration) of an antiperspirant active; (ii) 0–10% ethanol; (iii) additional water as required to adjust the refractive index; (iv) 0–5% of an antimicrobial agent; and (v) 0–5% of an ionizable salt; wherein the conductance of a water droplet applied to the surface of a thin film of the antiperspirant and/or deodorant composition is at least 250 micro Siemens/cm/ml as measured by a fixed geometry test at a loading of at least 7% by weight level of antiperspirant active.

30 Claims, No Drawings

HIGH OIL CLEAR EMULSION WITH DIENE ELASTOMER

FIELD OF THE INVENTION

This invention relates to clear antiperspirant and/or deodorant products which include an antiperspirant active ingredient and which provides better efficacy, stability and enhanced aesthetics. The compositions are emulsions made with an external (or oil) phase and an internal phase which contains the active ingredient. These emulsions may be used to form clear gel, soft solid or roll-on products.

BACKGROUND OF THE INVENTION

A large variety of antiperspirant and/or deodorant formulations have been described in the patent literature and/or have been made commercially available. These products have included suspension as well as emulsions. Also various physical forms may be used such as solids (for example, wax and sticks), semi-solids (for example, gels and creams), liquids (for example, roll-on products) and sprays (both aerosol and non-aerosol). In recent years a strong emphasis has been placed on improving both the performance and the aesthetics of these products. One of the particular problems is trying to obtain an emulsion product that has efficacy comparable to suspension products. A second problem is the stabilization of emulsion products to achieve a product that is shelf stable, but which releases an active ingredient in a timely manner.

With regard to emulsions, U.S. Pat. No. 4,673,570 to Soldati describes uniform, clear gelled antiperspirant compositions, free of waxes wherein the emulsions comprise in combination a volatile silicone fluid, a silicone emulsifier (such as a mixture of cyclomethicone and dimethicone copolyol), a destabilizing auxiliary emulsifier, water, a non-volatile emollient (such as C10–C20 alkyl fatty esters and ethers), linear silicone fluids, a coupling agent (such as low molecular weight alcohols and glycols), an active antiperspirant component and other ancillary agents.

U.S. Pat. No. 5,008,103 to Raleigh et al describes water-in-oil antiperspirant emulsions having a discontinuous polar phase containing water and optionally containing an emulsifier with a hydrophilic-lipophilic balance (HLB value) greater than 8, and a volatile silicone continuous phase with a dimethicone copolyol emulsifier. U.S. Pat. No. 5,401,870 to Raleigh et al and U.S. Pat. No. 5,292,503 to Pereira et al describe similar subject matter.

U.S. Pat. No. 5,216,033 to Pereira et al describes a transparent water-in-oil emulsion containing a silicone phase with a dimethicone copolyol and an aqueous phase containing a refractive index "transparency structurant" to produce a refractive index matched clear emulsion. The transparency structurant is a C3–C8 polyhydric alcohol.

U.S. Pat. No. 5,989,531 describes a liquid composition made with (a) an active phase comprising a selected glycol, a nonionic emulsifier having an HLB value greater than 8 and an antiperspirant and/or deodorant active; and (b) a silicone phase made with one or more of a dimethicone copolyols having an HLB less than 7 and nonionic emulsifiers having an HLB greater than 7, wherein the silicone phase has at least 10% silicone and the ratio of the silicone phase to the active phase is in the range of 1:1–1:4. Optional ingredients include the use of non-volatile silicones, volatile silicones and organic emollients.

U.S. Pat. No. 6,010,688 discloses the use of polyhydric alcohols to improve the stability and efficacy of antiperspirant formulations, particularly antiperspirant gels.

U.S. Pat. No. 5,955,065 discloses antiperspirant gel compositions containing soluble calcium salts. These compositions contain an aluminum or aluminum-zirconium antiperspirant salt and a water soluble calcium salt, both of which are suspended in a dermatologically acceptable anhydrous carrier vehicle. The present invention also embraces a method of inhibiting or reducing perspiration by topically applying an effective amount of such an antiperspirant composition to the skin.

U.S. Pat. No. 5,925,338 discloses a clear antiperspirant or deodorant gel composition which exhibits reduced staining while retaining excellent aesthetic attributes and efficacy. The oil phase comprises about 10 to 25% of the composition and contains a silicone oil and a polyether substituted silicone emulsifying agent. The silicone oil comprises a mixture of a non-volatile silicone, preferably a non-volatile linear silicone, and a volatile linear silicone. It has been found that reducing the amount of non-volatile silicone in the known gel composition to a relatively low level (e.g. below about 5%) and adding an amount of volatile linear silicone to the composition (e.g. above about 2%, preferably above about 5%) substantially improves the non-staining properties of the composition.

U.S. Pat. No. 5,623,017 discloses a clear silicone gel cosmetic composition with a water-containing internal phase. The silicone emulsifiers discussed are non-polymeric ethoxylated bis-trisiloxanes.

U.S. Pat. No. 6,007,799 discloses a clear cosmetic gel composition in the form of a water-in-oil emulsion, comprising (a) a water-based phase comprising water, a cosmetically active ingredient, and at least one coupling agent; and (b) an oil-based phase comprising a material having a refractive index in the range of 1.40–1.50, silicone fluids and an alkoxylated, alkyl substituted siloxane surface active agent (e.g., dimethicone copolyol). The composition has a refractive index in a range of 1.4026 to 1.4150. Where the cosmetically active ingredient is an antiperspirant active ingredient, the composition can be an antiperspirant gel (for example, soft gel) composition. In the refractive index range of the present invention, increased amounts of, for example, antiperspirant active ingredient, and other high-refractive-index materials providing cosmetic benefits, can be incorporated in the water and oil phases of the composition while still achieving a clear composition. The composition can also include polypropylene glycols (for example, tripropylene glycol), as part of the water-based phase, to provide a composition having reduced tackiness and reduced whitening (decreased residue); this composition is also mild.

U.S. Pat. No. 5,587,173 discloses a clear gel-type cosmetic product which has a viscosity of at least about 50,000 centipoise (cps) at 21° C., and includes an emulsion with an oil phase and a water phase that includes an incorporated active ingredient. The refractive indices of the water and oil phases match to at least 0.0004, the refractive index of the product is about 1.4000, and the product clarity is better than thirty NTU. These formulas contain 75–90% dispersed active phase. See also U.S. Pat. No. 4,021,536: which describes magnesium-zirconium complexes useful as antiperspirants; and U.S. Pat. No. 5,463,098 which describes clear antiperspirant gel stick and method for making same.

U.S. Pat. No. 3,979,510 describes aluminum-zirconium antiperspirant systems with complex aluminum buffers, including the use of various divalent metal ions in aluminum-zirconium antiperspirant formulations.

U.S. Pat. No. 4,980,156 discloses improved dry-feeling antiperspirant compositions which comprise an aqueous solution of an astringent emulsified in a volatile silicon fluid. The emulsion is stabilized by using a combination of a long-chain alkyl modified polysiloxane-polyoxyalkylene copolymer and an organic surfactant having an HLB value from 8 to 18.

U.S. Pat. No. 4,673,570 discloses uniform, clear gelled antiperspirant compositions, free of waxes and conventional gelling agents. The gel emulsions comprise, in combination, a volatile silicone fluid, a silicone emulsifier, a destabilizing auxiliary emulsifier, water, a non-volatile emollient, a coupling agent, an active antiperspirant component and ancillary agents.

U.S. Pat. No. 5,454,026 discloses a clear antiperspirant gel which is made by combining (a) an astringent compound having a refractive index of 1.48 to 1.53 which is an antiperspirant salt in the form of (i) a tray dried compound, (ii) an encapsulated salt, or (iii) a solvent solution of a salt compound; and (b) a clear anhydrous organic oil-free gel formed with 12-hydroxystearic acid as the gelling agent and a blend of aromatic containing silicone fluid and volatile silicone fluids.

U.S. Pat. No. 5,587,153 broadly discloses clear antiperspirant gels with a refractive index of 1.3975 to 1.4025 and a viscosity of 50,000–200,000 centipoise which are emulsions having 75–90% of a water phase.

U.S. Pat. No. 5,563,525 also discloses clear antiperspirant gels having a viscosity of at least 50,000 centipoise and a clarity better than 50 NTU which are emulsions having 75–90% of a water phase.

U.S. Pat. No. 6,060,546 to Powell et al describes a non-aqueous silicone emulsion containing a silicone phase and an organic phase in which the silicone phase contains a crosslinked silicone elastomer and the organic phase may contain up to 50% water.

U.S. Pat. No. 6,103,250 describes an anhydrous composition comprising 1–50% of a polar, emulsifying siloxane elastomer, 0.01–40% particulate material, and 1–70% of a nonpolar oil, wherein the elastomer is present in an amount to render the incompatible nonaqueous polar ingredient compatible in the anhydrous composition.

U.S. Pat. No. 5,922,308 to Brewster et al describes an underarm composition comprising 0.1–5.5% of a crosslinked non-emulsifying siloxane elastomer and 10–80% of volatile siloxane.

Historically, suspension products such as sticks have exhibited better efficacy than emulsion products. Previous attempts have not successfully overcome the problems of improving efficacy and achieving satisfactory formation of emulsions.

As an additional aspect of the invention, it has heretofore been difficult to obtain a clear emulsion when an elastomer was present. Also, it was been very difficult to get the elastomer to mix satisfactorily in an emulsion environment and the elastomer particles tend to still remain as isolated particles.

Examples of elastomer compositions include the following. PCT case WO 97/44010 and assigned to the same assignee as this application describes a silicone gel material made by combining (a) a volatile silicone material and (b) an organopolysiloxane material (or silicone elastomer) as a gelling agent wherein the organopolysiloxane material (silicone elastomer) can be a reaction product of a vinyl-terminated siloxane polymer and a silicon hydride cross-linking agent. Related technology is also disclosed in PCT case WO 98/00097, WO 98/00104 and 98/00105 assigned to Unilever PLC on cross-linked non-emulsifying elastomers.

U.S. Pat. No. 5,599,533 to Stepniewski et al assigned to Estee Lauder describes a stable water-in-oil emulsion system formed with an organopolysiloxane elastomer, a vehicle in which the elastomer is dispersed or dispersible, a stabilizing agent, a surfactant and an aqueous component. A commercial product known as "REVELATION" retexturizing complex for hands and chest sold by the same assignee contains a silicone gel material with an organopolysiloxane component and octamethylcyclotetrasiloxane. This reference does not teach a clear composition and also teaches that you have to cap the electrolyte at 5%. In addition, this reference relies on polyols and alcohols as stabilizing agents.

EP 0 787 758 A1 teaches a method for solvent thickening by using a silicone latex having a plurality of crosslinked polysiloxane particles.

Another recent case assigned to the same assignee as this application is WO 99/51192 and U.S. patent application Ser. No. 9/273152 which describes antiperspirant compositions with the use of broad categories of elastomers. Other examples of the use of elastomer type materials and/or methods for processing such materials may be found in PCT cases WO 98/00097; WO 98/00104; WO 98/00105; WO 98/18438; WO 98/42307 all of which are incorporated herein by reference.

Thus, it is an object of this invention to provide improved emulsions containing 25%–70% of an oil phase which exhibit improved efficacy which efficacy is comparable to that achieved in suspension products and, at the same time, have a stability profile that allows for satisfactory stability on the shelf. Another issue is the formation of emulsions which are stable on the shelf but which destabilize sufficiently after application to a skin surface so as to release an efficacious amount of an active ingredient. Thus, it is an object of the present invention to provide emulsions with those characteristics as well as enhanced aesthetics such as smoothness in application, low tack and dry feel. It is also an object of this invention to provide gel or soft solid compositions which can, if desired, be formed into clear compositions even with the presence of selected elastomer materials. It is still another object of this invention to provide compositions that can, if desired, be formed into clear compositions without the use of microemulsions.

SUMMARY OF THE INVENTION

This invention relates to a clear antiperspirant and/or deodorant composition in the form of a water-in-oil emulsion having a refractive index less than 1.42 and comprising:

(a) 25–70% (particularly with a high oil content of 25–50%, and more particularly 30–45%) of an external phase (also called the oil phase or the continuous phase) which is made with:

(i) 0.1–10% (on an actives basis) of at least one elastomer which is a cyclomethicone (and) dimethicone crosspolymer made with an $\equiv$Si—H containing polysiloxane and an alpha, omega-diene of formula $CH_2$=$CH(CH_2)_xCH$=$CH_2$, where x=1–20, to form a gel by crosslinking and addition of $\equiv$Si—H across double bonds in the alpha, omega diene, which crosspolymer has a viscosity in the range of 50,000–3,000,000 centipoise (particularly 100,000–1,000,000; more particularly 250,000–450,000 centipoise; and most particularly 350,000 centipoise), preferably with a nonvolatiles content of 8–18% (particularly 10–14% and most particularly 12–13%) in cyclomethicone (for example a D4 or D5 cyclomethicone), (an example of such a crosspolymer composition being DC-9040 from Dow Corning Corporation (Midland, Mich.) with other types of such crosspolymers (also called elastomers) being described in U.S. Pat. No. 5,654,362, incorporated by reference herein as to the description of such polymers and methods of making such polymers);

(ii) 0.1–5% (particularly 0.1–1.0%) of a silicone copolyol having an HLB value (hydrophilic lipophilic balance)$\leq 8$;

(iii) 0.1–68% of a volatile silicone selected in an amount to complete the external phase;

(iv) 0–10% (particularly 0–5%) of a cosurfactant or emulsifier having an HLB value in the range of 1–15;

(v) 0–5% of a non-volatile silicone; and (b) 30–75% (particularly 50–75%) of an internal phase (also called actives phase or dispersed phase) which is made with:

(i) 7–25% (on an anhydrous actives basis excluding the waters of hydration) of an antiperspirant active preferably added as a solution of active in water and/or water+glycol mixture as a solvent;

(ii) 0–10% ethanol;

(iii) additional water as needed to adjust the refractive index;

(iv) 0–5% of an antimicrobial agent; and (v) 0–5% of an ionizable salt;

wherein (1) the conductance of a water droplet applied to the surface of a thin film of the antiperspirant and/or deodorant composition is at least 250 micro Siemens/cm/ml as measured by the fixed geometry test described below at a loading of at least 7% by weight level of antiperspirant active (with more particular embodiments having conductances greater than 300 micro Siemens/cm/ml, particularly greater than 400 micro Siemens/cm/ml and especially greater than 500 micro Siemens/cm/ml.); and (2) all amounts are in percent by weight based on the total weight of the composition unless otherwise specified.

DETAILED DESCRIPTION OF THE INVENTION

The clear cosmetic compositions of this invention having a refractive index less than 1.42 are made with 25–70 (particularly 25–50% and, more particularly, 30–45%) of an external phase and 30–75% (particularly 50–75% and, more particularly, 55–70%) of an internal phase. Alternatively, another specific embodiment can include 40–70% and more particularly 50–60% of an external phase; and 30–60% and more particularly 40–50% of an internal phase.

The elastomer component described above is used in an amount of 0.1–10% (on an actives basis) particularly in an amount of 1–7% and, more particularly, in an amount of 1–5%. One particular elastomer of interest is DC 9040 from Dow Corning Corporation (Midland, Mich.). Frequently the elastomer is obtained as a mixture in cyclomethicone.

A silicone copolyol (especially dimethicone copolyol) may be used in an amount of 0.1–5% (actives basis), particularly 0.1–3% and, more particularly, 0.1–1.0%.

In general, silicone copolyols useful in the present invention include copolyols of the following Formulae I and II. Formula I materials may be represented by:

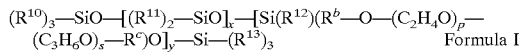

Formula I wherein each of $R^{10}$, $R^{11}$, $R^{12}$ and $R^{13}$ may be the same or different and each is selected from the group consisting of C1–C6 alkyl; $R^b$ is the radical $—C_mH_{2m}—$; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment $—(C_2H_4O)_p—(C_3H_6O)_s—$ has a molecular weight in the range of 200 to 5,000; the segment preferably having fifty to one hundred mole percent of oxyethylene units $—(C_2H_4O)_p—$ and one to fifty mole percent of oxypropylene units $—(C_3H_6O)_s—$; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical $—(CH_2)_3—$; and the values of p and s are such as to provide a molecular weight of the oxyalkylene segment $—(C_2H_4O)_p—(C_3H_6O)_s—$ of between about 1,000 to 3,000. Most preferably p and s should each have a value of about 18 to 28.

A second siloxane polyether (copolyol) has the Formula II:

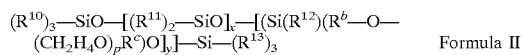

Formula II wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^3$ substituents which are attached to the two terminal silicon atoms at the end of the siloxane chain can be substituted with the segment $—R^b—O—(C_2H_4O)_p—(C_3H_6O)_s—R^c$ or with the segment $—R^b—O—(C_2H_4O)_p—R^c$. In some instances, it may be desirable to provide the segment $—R^b—O—(C_2H_4O)_p—(C_3H_6O)_s—R^c$ or the segment $—R^b—O—(C_2H_4O)_p—R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell, Va. Examples of specific products include DOW CORNING® 5225C from Dow Corning which is a 10% dimethicone copolyol in cyclomethicone; DOW CORNING® 2-5185C which is a 45–49% dimethicone copolyol in cyclomethicone; SIL WET L-7622 from Witco; ABIL EM97 from Goldschmidt which is a 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING® 2-5185 material is of particular interest.

In one particular embodiment 0.1–5% (particularly 1.0–5.0%) of a 10–50% silicone copolyol such as dimethicone copolyol in cyclomethicone mixture may be used, wherein the amount of mixture added is selected so that the level of silicone copolyol in the cosmetic composition is in the range of 0.25–5.0% (particularly 1%) (for example, 0.25–10% of a 40%–50% dimethicone copolyol in cyclomethicone mixture).

For the volatile silicone component, an amount of 0.1–68% may be used plus an incremental amount to complete the selected amount of the external phase (quantum sufficient or "q.s."). Particular ranges include 10–58%, (more particularly 10–50% and, even more particularly, 15–30%) by weight based on the entire weight of the composition which may be used. By volatile silicone material is meant a material that has a measurable vapor pressure at ambient temperature. For the volatile silicone portion, examples of volatile silicones (particularly silicones with a boiling point of 250 degrees C. or less at atmospheric pressure) include cyclomethicone (especially cyclopentasiloxane, also called "D5"), "hexamethyldisiloxane", and low viscosity dimethicone (for example, Dow Corning® 200 fluid having a viscosity of 1–200 centistokes). Such volatile silicones include conventional cyclic and linear volatile silicones Illustratively, and not by way of limitation, the volatile silicones are one or more members selected from the group consisting of cyclic polydimethylsiloxanes such as those represented by Formula III:

Formula III

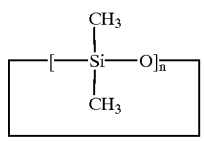

where n is an integer with a value of 3–7, particularly 5–6. For example, DC-245 fluid (or the DC-345 version) from Dow Corning Corporation (Midland, Mich.) is a type of cyclomethicone which can be used. These include a tetramer (or octylmethylcyclotetrasiloxane) and a pentamer (or decamethylcyclopentasiloxane). The volatile linear silicones can also be included in this group of volatile silicones and are one or more members selected from the group consisting of linear polydimethylsiloxanes such as those represented by Formula IV:

Formula IV

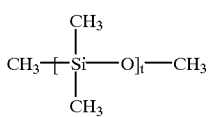

and t is selected to obtain a viscosity of 1–200 centistokes.

The co-surfactants used in this invention (which can also be a mixture or blend of surfactants) include, but are not limited to at least one member selected from the group consisting of:

(a) sorbitan esters and ethoxylated sorbitan esters (for example PEG-20 sorbitan isostearate, sorbitan monolaurate, polysorbate-20, polysorbate-40, polysorbate-60, polysorbate-80);

(b) ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, and Oleath-20);

(c) ethoxylated adducts (for example, PEG-25 stearate, glyceryl stearate and PEG-100 stearate);

(d) PEG esters (for example, PEG-8 oleate, PEG-8 laurate, PEG-8 dilaurate, PEG-12 dilaurate, PEG-80 diisostearate, PEG-40 stearate);

(e) propoxylates (for example, PPG-10 butanediol, PPG-50 oleyl ether, PPG-2-ceteareth-9, PPG-3-deceth-3, PPG-5-ceteth-20);

(f) ethoxylated modified triglycerides (for example, PEG-20 corn glycerides, PEG-12 palm kernel glycerides);

(g) alkylphenol aromatic ethoxylates (for example, dinonylphenol ethoxylate with 9 moles of EO, octylphenol ethoxylate with 20 moles of EO, octylphenol ethoxylate with 40 moles of EO); and (h) block copolymers which are alkoxylated glycols having ethoxylated and propoxylated segments (for example, Poloxamers 182 and 234, and Meroxapol 174); wherein the nonionic surfactant is selected so that it has an HLB (hydrophilic-lipophilic balance) value in the range of 1–15.

The HLB parameter is a well known parameter the calculation of which is disclosed and explained in numerous references. For nonionic surfactants, data obtained by actual analysis is usually a more accurate measure of HLB values (rather than theoretical determinations). For purposes of this invention it is intended that either the actual or theoretical HLB value may be used as the basis for selection.

For the co-surfactant having an HLB value $\leq 8$, examples include:

(a) ethoxylated alcohols such as steareth-2, Oleth-3, nonoxynol-2, PPG-4-Ceteth-1;

(b) ethoxylated carboxylic acids such as PEG-4 dilaurate, PEG-2 oleate;

(c) glyceryl esters such as PEG-2 castor oil, PEG-7 hydrogenated castor oil, glyceryl monooleate, glyceryl monostearate, triglycerol monooleate, decaglyceryl tetraoleate, and polyglyceryl-3 oleate, glyceryl stearate;

(d) sorbitan derivatives such as sorbitan oleate, sorbitan monostearate, sorbitan tristearate, sorbitan monooleate, sorbitol trioleate, sorbitan monotallate, sorbitan isostearate;

(e) sugar esters such as sucrose distearate; and (f) lanolin alcohol.

The surfactant or blend of surfactants incorporated into the compositions of the present invention can, illustratively, be included in amounts of 0.1–20%, preferably 0.5–10%, and more preferably 1–5%, by weight based on the total weight of the composition.

The non-volatile silicone component may be used as an optional emollient or to match the refractive index. Examples of non-volatile silicones (that is, silicones with a boiling point above 250 degrees C. at atmospheric pressure) include phenyl trimethicone, dimethicone, phenylpropyltrimethicone (SF1555 from General Electric, Waterford, N.Y.), cetyl dimethicone, and dimethiconol as well as two or more of the forgoing.

For the antiperspirant active used in the internal (also called "active") phase various antiperspirant active materials that can be utilized according to the present invention provided that they are soluble at a suitable concentration in the active phase. These include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein. Particular actives include Westchlor A2Z 4105 aluminum zirconium tetrachlorohydrex gly propylene glycol complex, (from Westwood Chemical Corporation, Middletown, N.Y.); Westchlor ZR 35B aluminum zirconium tetrachlorhydrex gly, and Rezal 36 GP and AZP 902 aluminum zirconium tetrachlorhydrex gly both from Reheis, Berkeley Heights, N.J. as well as Rezal AZZ 908 from Reheis. In general, the metal:chloride mole ratio is in the range of 2.1–0.9:1 for such salts.

Actives of special interest because they form low RI solutions include: Westchlor Zr 35BX3 (30–35% actives in water) from Westwood Chemical Company, Middletown, N.Y.; Rezal 36G (46% in water) from Reheis Inc., Berkeley Heights, N.J.; Summit AZG-368 (28–32% in water) from Summit Research Labs, Huguenot, N.Y.; Reach 301 (39% in water) from Reheis Inc.; and aluminum chloride (28% in water) which may be obtained from several sources. In general, the metal:chloride mole ratio is approximately 1.4:1 for such salts.

In one particular type of salt of interest, an aluminum zirconium tetra salt with glycine is used wherein aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium mole ratio greater than 1.3:1, particularly greater than 1.4:1. This type of salt may be made in a variety of ways as described in co-pending case IR 6558 filed on the same day as this application.:

Method A: An aluminum chlorohydrate (ACH) solution of ACH salt in water of suitable concentration is mixed with an aqueous solution of zirconyl chloride ($ZrOCl_2$) of suitable concentration and powdered glycine. The mixture is stirred at room temperature to obtain the salt.

Method B: A suitable commercially available aluminum zirconium tetrachlorohydrex glycine salt is obtained and mixed with a sufficient amount of an aqueous aluminum chloride ($AlCl_3$) solution and powdered glycine. The mixture is stirred at room temperature to obtain the salt. When Method B is used, a suitable salt to use as a starting material includes various types of tetra salts such as aluminum zirconium tetrachlorohydrex gly, aluminum zirconium tetrachlorohydrex gly propylene glycol complex, aluminum zirconium tetrachlorohydrex gly dipropylene glycol complex, and mixtures of any of the foregoing . These salts will be referred to hereinafter as experimental salts or carry an "exp" suffix in their designation. It is preferred that the experimental salt be used in the form of a 28–50% water solution when added to form the compositions of the invention.

Method C: An aqueous aluminum chlorohydrate (ACH) solution made from an activated ACH salt of suitable concentration is mixed with an aqueous solution of zirconyl chloride ($ZrOCl_2$) of suitable concentration and powdered glycine. The mixture is stirred at room temperature for a short period of time and then spray dried to obtain the salt in powder form.

Mixtures of actives can also be used, provided a suitable amount of low RI material is used to achieve a satisfactory product.

Antiperspirant actives can be incorporated into compositions according to the present invention in amounts in the range of 7–25% (on an anhydrous solids basis), preferably 7–20%, by weight, of the total weight of the composition. The amount used will depend on the formulation of the composition. At amounts at the higher end of the range (especially in a range of 9–20% or 9–25%, a good antiperspirant effect can be expected. As noted above, the active is preferably included in the compositions of the invention by premixing the active with water and possibly small amount of propylene glycol.

Deodorant active materials can also be included such as:
(a) fragrances, such as in the range of 0.5–3.0 percent by weight based on the total weight of the composition;
(b) effective amounts of antimicrobial agents, for example, 0.05–5.0 percent (particularly 0.1–1% and, more particularly, 0.25–1.0%) by weight based on the total weight of the composition; examples include bacteriostatic quaternary ammonium compounds (such as cetyl trimethyl-ammonium bromide, and cetyl pyridinium chloride), 2,4,4'-trichloro-2'- hydroxydiphenylether (Triclosan), N-(4-chlorophenyl)-N'-(3,4-dichlorophenyl) urea (Triclocarban), silver halides, octoxyglycerin (SENSIVA™ SC 50) and various zinc salts (for example, zinc ricinoleate). Triclosan or Triclocarban can, illustratively, be included in an amount of from 0.05% to about 0.5% by weight, of the total weight of the composition; or (c) effective amounts of a masking agent, such as 0.1–5%.

While it has been described that the water component of the invention may also contain a minor amount of a glycol component such as propylene glycol, it is preferred that no added glycol be used. The glycol component, if included, is comprised of one or more glycols and/or a polyglycols selected from the group consisting of ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component include one or more members of the group consisting of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Propylene glycol is of particular interest because the antiperspirant active is more soluble in this type of glycol. Tripropylene glycol has lower irritancy, but the antiperspirant active is not as soluble in this glycol. Methyl propylene glycol is also of interest. Mixtures of glycols may be used to balance these desirable properties.

The compositions of the present invention can also include other optional ingredients to improve the aesthetics and/or performance of the cosmetic compositions of the invention. These include emollients, thickeners, colorants, fillers, fragrances, masking agents, etc.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula VI:

Formula VI

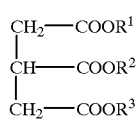

wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4CO$—$OR^5$. The chain length for $R^4$ and $R^5$ can vary from 7 to 30 and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated fatty acids which are the carboxylic acids obtained by hydrolysis of animal or vegetable fats and oils. These have general structure $R^6COOH$ with the $R^6$ group having a carbon chain length between 7 and 30, straight chain or branched. Specific examples include lauric, myristic, palmitic, stearic, oleic, linoleic and behenic acid.

(e) saturated and unsaturated fatty alcohols (including guerbet alcohols) with general structure $R^7COH$ where $R^7$ can be straight or branched and have carbon length of 7 to 30. Specific examples include lauryl, myristyl, cetyl, isocetyl, stearyl, isostearyl, oleyl, ricinoleyl and erucyl alcohol;

(f) lanolin and its derivatives which are a complex esterified mixture of high molecular weight esters of (hydroxylated) fatty acids with aliphatic and alicyclic alcohols and sterols. General structures would include $R^8CH_2$—$(OCH_2CH_2)_n OH$ where $R^8$ represents the fatty groups derived from lanolin and n=5 to 75 or $R^9CO$—$(OCH_2CH_2)_n$ OH where $R^9CO$- represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(g) alkoxylated alcohols wherein the alcohol portion is selected from aliphatic alcohols having 2–18 and more particularly 4–18 carbons, and the alkylene portion is selected from the group consisting of ethylene oxide, and propylene oxide having a number of alkylene oxide units from 2–53 and, more particularly, from 2–15. Examples include cetyl glyceryl ether; isostearyl glyceryl ether; isostearyl glyceryl pentaerythrityl ether;

laureth-5 butyl ether; oleyl glyceryl ether; PEG-4 ditallow ether; polyglyceryl-3 cetyl ether; polyglyceryl-4 lauryl ether; PPG-9 diglyceryl ether; propylene glycol myristyl ether. More specific examples include PPG-14 butyl ether, PPG-53 butyl ether laureth-5 butyl ether and PEG-4 ditallow ether.

(h) ethers selected from the group consisting of dicaprylyl ether; dicetyl ether; dimethyl ether; distearyl ether; ethyl ether; isopropyl hydroxycetyl ether; methyl hexyl ether; polyvinyl methyl ether;

(i) silicones and silanes the linear organo-substituted polysiloxanes which are polymers of silicon/oxygen with general structure:

(1) $(R^{10})_3SiO(Si(R^{11})_2O)_xSi(R^{12})_3$ where $R^{10}$, $R^{11}$ and $R^{12}$ can be same or different and are each independently selected from the group consisting of phenyl and C1–C60 alkyl;

(2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting of phenyl and C1–C60 alkyl; or (3) organo substituted silicon compounds of formula $R^{17}Si(R^{18})OSiR^{19}$ which are not polymeric where $R^{17}$, $R^{18}$ and $R^{19}$ can be the same or different and are each independently selected from the group consisting of phenyl and C1–C60 alkyl optionally with one or both of the terminal R groups also containing an hydroxyl group. Specific examples include dimethicone, dimethiconol behenate, $C_{30-45}$ alkyl methicone, stearoxytrimethylsilane, phenyl trimethicone and stearyl dimethicone.

(j) adipic acid blends selected from the group consisting of trimethyl pentanediol/adipic acid copolymer (LEXOREZ TL8 from Inolex, Philadelphia, Pa.); trimethyl pentanediol/adipic acid/isononanoic acid copolymer (LEXOREZ TC8); and adipic acid/diethylene glycol/glycerin crosspolymer (LEXOREZ 100);

(k) mixtures and blends of two or more of the foregoing.

Particular examples of suitable emollients include members of the group consisting of Octyloxyglyderin (SENSIVA SC50 from Schülke Mayr, Norderstedt, Germany) (which can be used as an emollient as well as an antibacterial); Polysorbate 80 (TWEEN 80 from ICI Americas, Wilmington, Del.); Oleth-20; ethoxylated alcohols such as steareth-2, nonoxynol-2, PPG-4-Ceteth-1; ethoxylated carboxylic acids such as PEG-4 dilaurate, PEG-2 oleate; glyceryl esters such as PEG-2 castor oil, polyglyceryl-3 oleate, glyceryl stearate; sorbitan derivatives such as sorbitan oleate; PPG-3 myristyl ether (such as WITCONOL APM from Goldschmidt), a dimethiconol (such as Dow Coming® DC1501 dimethiconol), neopentyl glycol diheptanoate, PEG-8 laurate, isocetyl stearate, dimethicone copolyol laurate, Dow Corning 2501 cosmetic wax (dimethicone copolyol); isostearyl isostearate, isostearyl palmitate, isostearyl alcohol, PPG-5-ceteth-20, PPG-10-cetyl ether, triethyl hexanoin, ethyl hexyl isostearate, glyceryl oleate, and isopropyl isostearate.

The emollient or emollient mixture or blend thereof incorporated in compositions according to the present invention can, illustratively, be included in amounts of 0.5–50%, preferably 1–25%, more preferably 3–5%, by weight, of the total weight of the composition.

As described above, water is used to make the solution of antiperspirant active and an additional amount of water may be added as needed to adjust the refractive index. The total amount of water from all sources may be present, for example in the range of 15–55%, particularly 40–55%. In a further optional aspect of the invention, the water also may comprise up to 5% (based on the entire composition) of an ionizable salt of the form $M_aX_b$ where a=1 or 2; b=1 or 2; M is a member selected from the group consisting of $Na^{+1}$, $Li^{+1}$, $K^{+1}$, $Mg^{+2}$, $Ca^{+2}$, $Sr^{+2}$, $Sn^{+2}$, and $Zn^{+2}$; and X is a member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, malonate, maleate, succinate, carbonate, bicarbonate, sulfate and hydrogensulfate. A salt of particular utility is NaCl. As will be appreciated by those skilled in the art, while it may be possible under certain circumstances to add a salt directly to a portion of the mixture during manufacturing, it is preferred to add the salt as a mixture or solution of the salt in a carrier or solvent, particularly water. Of course, various concentration of the salt can be made such as in the range of 1–40%, particularly 10–30% and, more particularly, 25–30%.

The stability of the emulsions of the invention may be measured by (1) visually evaluating the emulsions for phase separation and (2) for gels, further monitoring the rheology using the viscosity tests described below.

The compositions of the present invention can include other optional ingredients to improve the aesthetics and/or performance of the cosmetic compositions of the invention. These include colorants, fillers, fragrances, emollients, masking agents, water soluble emollients, hydrogen bonding modifiers (for example, urea, guanidine hydrochloride, xylitol, trehalose, maltose and glycerine), additional fragrances, additional preservatives, etc. Such one or more other optional ingredients can be added to the internal or external phases or both in appropriate amounts. For example, fragrances will frequently be partitioned to both the external and internal phases regardless of when or to what phase (or final product) the fragrance is added.

In a preferred embodiment the refractive indices of the external and internal phases are matched within 0.005 to obtain a clear product.

The release of antiperspirant actives into the sweat is a significant event in the development of an antiperspirant effect. The magnitude of the antiperspirant effect is related to the concentration of the antiperspirant salt in the sweat, and therefore measuring the concentration of antiperspirant salt can provide an estimate of antiperspirant efficacy. A variety of methods can be used to evaluate antiperspirant salt concentration, ranging from atomic absorption, ICP, and HPLC to solution conductance of aqueous films. The later method is especially well suited for measuring the release of small amounts of antiperspirant salts. The methods outlined below use solution conductance to estimate antiperspirant salt release upon short exposures to deionized water.

As noted above, the conductance of the compositions of the invention is defined with reference to a value of at least 250 micro Siemens/crn/ml when the composition is loaded with at least 7% of an antiperspirant active (such as the antiperspirant actives listed above) and when the conductance is measured by a fixed geometry test. For purposes of clarification it should be explained that there are a variety of tests and test conditions that can be used to evaluate:

(1) "Conductance" is defined as an absolute measure of current flow through a solution with the dimensions of micro Siemens/cm, which value is independent of probe geometry. This value is divided by the volume (in ml) of applied water to give the conductance number with the units of micro Siemens/cm/ml. This test is deemed a more reproducible measurement since it references a set of fixed dimensions and units.

(2) Alternatively, "conductivity" as a measure of current flow through a solution without reference to probe geometry, and which is measured in micro Siemens.

This test is convenient for quick screening of solutions.

Standard Test for Thin Film Conductivity

One test for conductivity is called herein the "standard" test. A non-conducting plastic block (for example, made from PLEXIGLASS® material) to form an oval shaped well 12.2 cm×2.5 cm with a depth of 100 microns. This depth corresponds to the mean thickness of an antiperspirant product applied to the underarm of a human person during real use conditions (approximately 50 to 100 microns). An aliquot of test sample is placed in the well of the block sufficient to fill the well to the brim. Excess sample is scraped off by running a flat edged instrument over the surface of the block. The sample block, with the product film, is then either (a) equilibrated at room temperature for two hours or (b) placed in a synthetic underarm to simulate in vivo conditions. If method (b) is used, the air temperature inside the synthetic underarm is maintained at 33 to 35° C. and a relative humidity of 85 to 95%, and the sample blocks are placed on a temperature controlled surface maintained at body temperature (37° C.). These conditions closely approximate the temperature gradients normally found in the underarm. Samples are equilibrated in either the (a) or (b) environments for two hours prior to measurement of antiperspirant salt release by solution conductivity. After two hours the sample blocks are removed from the controlled environment and placed on a stage for conductivity measurement. An aliquot of 250 microliters of water with a resistance of at least 17 mega ohms is placed on the surface of the sample film, and the conductance of the water is measured as a function of time with a Skicon 200 Skin surface Hygrometer (I.B.S. Co., Ltd., Shizuoka-ken, 430, Japan) using an Elsnau (MT-8C Probe) electrode (Todd Maibach & Associates, San Francisco, Calif.). The electrode is positioned so that it touches the bottom of the test sample in the well. Conductivity is measured in micro Siemens at 3.5 MHz. Data is collected at 0.1 sec intervals for approximately 100 sec. Solution conductivity after 10 seconds of exposure to the water is used to compare the release of active salt for different formulations This method is believed to be particularly useful for evaluating the release of antiperspirant salts in the absence of other salts. The standard method is useful as a quick screening tool for active salt release studies. A solution conductivity of approximately 400 or greater micro Siemens at 10 sec after application of the water droplet to the surface of the test sample, can be considered evidence of significant release of the antiperspirant active salt from the film surface and correlates with improved antiperspirant efficacy.

Fixed Geometry Test for Thin Film Conductance

One of the limitations of the Standard Test is that the area of the water droplet is not controlled and, therefore, the apparent conductance (which is measured as conductivity because the water volume is not controlled) is dependent on droplet spreading. This will lead to an underestimate of the actual solution conductance (and therefore antiperspirant salt release), of water drops which spread significantly. In order to measure the absolute concentration of the antiperspirant salts the spreading of the water drop must be stopped. This can be accomplished by placing a well of know dimensions on the surface of the product film to establish an area of constant size that is exposed to the water droplet. A more predictable test is needed, such as the Fixed Geometry Test.

The Fixed Geometry Test uses the same basic technique as the Standard Test in terms of preparation of the test well, addition of the test sample and equilibration of the sample to a selected temperature. Instead of allowing the water to flow freely on the surface of the test film, however, a second structure of non-conducing plastic predrilled with holes of a fixed diameter is clamped over the well block. The second structure with holes is also made of a non-conducting material (such as PLEXIGLAS material), is open on both ends and has an internal diameter of 1.905 cm. The bottom of each predrilled hole is fitted with a small O-ring to prevent leakage of the water. A 400 microliter aliquot of water (rather than the 250 microliter aliquot used in the Standard Test) with a resistance of 17 mega Ohms is then placed in the hole to cover the test sample. This will normally result in a liquid height for water of about 1.4 mm. The Elsnau probe is positioned through the drilled hole so that the bottom of the probe rests on the bottom of the well at a right angle. Because of the fixed shape, data can be obtained as conductance in micro Siemens/cm/ml using the method described for calculation.

As will be appreciated by those skilled in the art, a variety of other shapes, sizes and orientations of electrodes can be used. In another variation on the Fixed Geometry Test, thin gold wires (99% purity, set of 2, each about 1 mm in diameter) can be constructed to be in parallel with the surface of the water (and covered by the water) and conductance can be measured.

The electrode used in both types of tests must be calibrated so that a conductivity in micro Siemens can be obtained. Such calibration with a salt solutions in water of known conductance is known to those skilled in the art.

While different readings can be obtained depending on the thickness of the films, the test used, etc. it is important to establish a standard test for purposes of defining conductivity according to this invention. The Fixed Geometry Test is set as the defining test because it is believed to be more reproducible. Thus a minimum conductance value of 250 micro Siemens/cm/ml is the lower limit. Interestingly, minimum values for the Standard Test seemed to run about 400 micro Siemens due to the way the test was conducted. For the data described here, samples should be placed in a chamber at the humidity and elevated temperature conditions described above for about 2 hours. Samples not subjected to elevated temperatures should give higher values.

An average efficacy gel having a water content of greater than 35% (such as Gillette's Right Guard Antiperspirant Gel) was compared with an improved gel made according to Example 12 below. The average efficacy gel has a standard conductivity of 295±35 micro Siemens at 10 seconds and a fixed geometry conductivity of 121±47 micro Siemens/cm/ml at 10 seconds. The improved formulation made according to this invention had a standard conductivity of 3554 micro Siemens at 10 seconds. The improved formulation was ranked as above average in efficacy in a forearm test whereas the average gel was ranked as average in efficacy in a clinical test.

While it is not known precisely how the compositions of this invention work, it has been observed that they have a combination of two important properties. These compositions exhibit superior stability on the shelf and yet degrade on contact with the skin to release the active ingredient with a higher level of efficacy than is usually achieved. The deodorant and/or antiperspirant compositions disclosed in this invention form metastable emulsions when deposited on the skin. The decomposition of these emulsions upon application can be assessed by the thin film conductance method described herein.

Particular formulations of interest include:

Formulation A
- 0.5–2.5% dimethicone copolyol (for example, Dow Corning 2-5185C (48%))
- 55–65% elastomer in cyclomethicone (for example, DC 9040 from Dow Corning)
- 1–10% PPG-3 myristyl ether
- 10–25% antiperspirant active (for example, Westchlor Zr 35 BX3 or Summit AZG-368)
- 10–25% water
- 0.5–1.5% fragrance Formulation B
- 1.0–3.0% dimethicone copolyol (for example, Dow Corning 2-5185C (48%))
- 40–60% elastomer in cyclomethicone (for example, DC 9040 from Dow Corning)
- 1–5% cyclomethicone (in addition to that found in the elastomer)
- 4–12% PPG-3 myristyl ether
- 15–30% antiperspirant active (for example, Westchlor Zr 35 BX3 or Summit AZG-368)
- 15–35% water
- 0.5–1.5% fragrance Formulation C
- 1.0–3.0% dimethicone copolyol (for example, Dow Corning 2-5185C (48%))
- 1–10% hydrogenated polyisobutene (for example, Fancol™ Polyiso 250)
- 40–55% elastomer in cyclomethicone (for example, DC 9040 from Dow Corning)
- 3–8% PPG-3 myristyl ether
- 15–20% antiperspirant active (for example, Westchlor Zr 35 BX3 or Summit AZG-368)
- 20–30% water
- 1.0–3.0% fragrance Formulation D
- 1.0–3.0% dimethicone copolyol (for example, Corning 2-5185C (48%))
- 40–60% elastomer in cyclomethicone (for example, DC 9040 from Dow Corning)
- 3–8% PPG-3 myristyl ether
- 15–30% antiperspirant active (for example, Westchlor Zr 35 BX3 or Summit AZG-368)
- 15–30% water
- 0.5–1.5% fragrance
- 1–10% diethylhexyl naphthalate Formulation E
- 0.5–2.5% dimethicone copolyol (for example, Dow Corning 2-5185C (48%))
- 60–70% elastomer in cyclomethicone (for example, DC 9040 from Dow Corning)
- 7–10% antiperspirant active (for example, Westchlor Zr 35 BX3 or Summit AZG-368)
- 25–35% water
- 1–10% methylpropylene diol (MPDiol)
- 0.5–1.5% fragrance Formulation F
- 1.0–3.0% dimethicone copolyol (for example, Dow Corning 2-5185C (48%))
- 6–10% hydrogenated polyisobutene (for example, Fancol™ Polyiso 250)
- 35–45% elastomer in cyclomethicone (for example, DC 9040 from Dow Corning)
- 6–10% PPG-3 myristyl ether
- 40–50% antiperspirant active as 43% active in water (for example, active is Westchlor Zr 35 BX3 or Summit AZG-368)
- no additional water
- 0.5–1.0% fragrance Formulation G
- 0.1–0.6% dimethicone copolyol (for example, Corning 2-5185C (48%))
- 4–7% hydrogenated polyisobutene (for example, Fancol™ Polyiso 250)
- 40–50% elastomer in cyclomethicone (for example, DC 9040 from Dow Corning)
- 4–7% PPG-3 myristyl ether
- 40–50% antiperspirant active as 43% active in water (for example, active is Westchlor Zr 35 BX3 or Summit AZG-368)
- no additional water
- 0.5–1.0% fragrance Formulation H
- 0.5–2.0% dimethicone copolyol (for example, Dow Corning 2-5185C (48%))
- 1–7% hydrogenated polyisobutene (for example, Fancol™ Polyiso 250)
- 40–50% elastomer in cyclomethicone (for example, DC 9040 from Dow Corning)
- 45–55% antiperspirant active as 43% active in water (for example, active is Westchlor Zr 35 BX3 or Summit AZG-368)
- no additional water
- 0.5–1.5% fragrance Formulation I
- 2–7% dimethicone copolyol (for example, Dow Corning 2-5185C (48%))
- 0.1–1% Oleath-20
- 1–5% C12–15 alkyl benzoate (Finsolv TN)
- 15–40% elastomer in cyclomethicone (for example, DC 9040 from Dow Corning)
- 15–25% antiperspirant active (for example, active is Westchlor Zr 35 BX3 or Summit AZG-368)
- 15–30% water
- 0.5–1.5% fragrance The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For roll-ons the compositions can be placed in a conventional type of container. This provides good deposition of the active material on the skin.

Compositions of the present invention can be formulated as clear, translucent or opaque products, although clear products are preferred. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present invention, there are differences between transparent (clear), translucent and opaque compositions.

Compositions of the present invention may be made by the techniques described in the Examples below. In general, the external and internal phases are formed separately using heating with the addition of a non-ionic emulsifier as needed. The alcohol component is added to the internal phase. The internal phase is added to the external phase very slowly. After the addition has been completed, the mixture is stirred at speeds on the order of 250–1000 rpm (for example, 700 rpm), to achieve a homogeneous mixture, followed by homogenization at speeds which are correlated with a voltage setting of about 55–65, particularly 60, on a Powerstat Variable Autotransformer to achieve the target viscosity. Compositions with a viscosity of 0–50,000 centipoise, especially 5,000–20,000 centipoise, may be suitable for roll-on products while compositions having a viscosity on the order of 50–400,000 centipoise may be more suitable for soft solids or creams.

A variety of equipment and techniques may be used to obtain the compositions of the invention, including one pass homogenization, colloidal mill. Examples of such equipment include Sonic Production Sonolator 200-30, and Sonic Tri-Homo Colloid Mill both of which may be obtained from Sonic Corporation, Stratford, Conn.

It is believed that the more homogeneous the composition is and the more uniform the particle size, the better properties of the composition.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

EXAMPLES

The following Examples are offered as illustrative of the invention and are not to be construed as limitations thereon.

In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. If alcohol is used, it is 95% unless otherwise indicated. Unless otherwise indicated, "water" or "D.I. water" mean deionized water. As is true throughout the application, the amounts of the components are in weight percents based on the standard described; if no other standard is described then the total weight of the composition is to be inferred. Various names of chemical components include those listed in the CTFA International Cosmetic Ingredient Dictionary (Cosmetics, Toiletry and Fragrance Association, Inc., $7^{th}$ ed. 1997). Viscosities are measured using Brookfield viscometers unless otherwise indicated. While specific amounts of particular elastomers have been described, there are chemical differences in the variety of elastomers that are available. The use of different elastomers may result in the need to increase or decrease the amount of elastomer used in a particular formulation, especially if a clear product is desired.

Example 1

General Method

In general, the external and internal phases are formed separately either at room temperature or with heating as described below. The internal phase is added to the external phase very slowly while stirring at to form an emulsion. After the addition has been completed, the mixture is stirred at higher speed to achieve a homogeneous mixture. The final formula viscosity is then achieved by homogenizing the emulsion under either batch or continuous process conditions as described below. The fragrance may be added at any time during the process prior to final homogenization.

Preparation of the External Phase

The ingredients to be used in the external phase (including the elastomer) are weighed out at room temperature and combined in a suitable vessel such as a 2 liter glass beaker. The mixture is stirred at about 500 rpm for 15–20 minutes using an overhead mixer such as a Lightnin Mixer Model L1003. If a waxy or solid emollient is to be added to the external (also called "continuous") phase, the mixture may be heated to facilitate dissolution while stirring then cooled to room temperature prior to combination with the internal phase as described below. The elastomer component is obtained as a suspension of elastomer in cyclomethicone (for example at a concentration of 6% active in D5 cyclomethicone). The elastomer component is added to the external phase with stirring at high speed (500–700 rpm for a 0.5 kilogram batch) until no particles of elastomer are visible to the eye.

Preparation of the Internal Phase

The internal dispersed phase is prepared as described below. Ingredients are mixed for a time sufficient to achieve homogeneity. The antiperspirant active used (for example, Westchlor Zr 35 BX3 (for example, 43% aluminum-zirconium glycinate in water) is weighed into a large beaker equipped with an overhead stirrer. Other internal phase ingredients are then added while stirring.

The fragrance (if any is used) is added last and may be added to the external phase normally (although it may be added to either the external phase or the internal phase if alcohol is used in the formulation) or the final formula prior to homogenization. For many of the examples described here, one could add the fragrance to the external phase.

If an optional non-ionic emulsifier such as Oleath-20 is used, the emulsifier and propylene glycol are combined in a separate beaker and heated to 40 degrees C. with stirring until the non-ionic emulsifier completely dissolved. The heat is turned off and the remaining ingredients to be used in the internal phase, including the antiperspirant active are weighed out and added to the mixture of propylene glycol and non-ionic emulsifier.

If water or a salt solution are used, the internal phase is prepared as follows. The solution containing antiperspirant active salt as received from supplier is weighed into a large beaker equipped with a magnetic stirrer. Additional ingredients such as propylene glycol, ethanol and water are added while stirring. If a salt water solution is used (such as for NaCl, etc.), the salt water solution is prepared by dissolving the crystalline salt in water in a separate beaker and stirring until dissolved. The salt water solution is then added to the rest of the internal phase and the mixture is stirred until homogeneous.

Preparation of the Emulsion

The internal phase made as described above is then added to the external phase over the course of 15–30 minutes while stirring at a speed of 500–700 rpm. After the addition is complete, the mixture is stirred at 500–700 rpm for 20 minutes using a Lightnin Mixer Model L1003. The mixture is then homogenized for 2–4 minutes (especially 3 minutes) using a homogenizer from Greerco Corp., Hudson, N.H. at a reading of about 60 on a Powerstat Variable Autotransformer from Superior Electric Co., Bristol, Conn.

Further Processing

The product is then further processed by homogenization to achieve the desired final viscosity. This can be done by using a Gilford-Wood Model 1-L (Greerco Corp., Hudson, N.H.) homogenizer. The homogenizer speed is controlled by a Powerstat Variable Autotransformer Type 3PN116B (Superior Electronic. Co., Bristol, Conn.). Typical voltage setting and processing time are chosen to give a desired final formula viscosity.

An other method of homogenization of the final product is to pass the emulsion through a colloid mill such as a Sonic Tri-Homo Colloid Mill or a process sonolator such Sonic Production Sonolator 200-30 both available from Sonic Corporation of Stratford, Conn. Process conditions are chosen to give the desired final product viscosity.

Example 2

Evaluation of Viscosity

Brookfield Viscosity

Viscosity can be measured using a Brookfield instrument (Model DV11+) with an E Spindle at 2.5 revolutions per minute (rpm) and a setting of S 95. Units are in centipoise ("cps").

Carri-Med Viscosity p A second way of evaluating rheology is with the use of Carri-Med equipment to obtain complex viscosity. Rheological parameters can be measured using a Carri-Med CSL 100 instrument with parallel plates. Initially the zero gap is set on the instrument. A sample of approximately 5 grams is placed on the stage of the instrument. A 15 minute compression is used for sample equilibration. The excess of the sample is scraped around the plate geometry. The rheological parameters G, G", tan (delta) and complex viscosity (n*) can be measured by torque sweep experiments. An acrylic plate 6 cm in diameter can be used. A gap (1000 microns) is used between the two plates (acrylic plates 6 cm in diameter). Temperature is maintained at 23 degrees C. The oscillation stress can be varied from 2.358 Pa to 50.74 Pa with an oscillation frequency kept constant at 1 Hertz. Units are in Pascal seconds ("Pa sec").

TABLE A

| Ingredient | Ex. 3 | Ex. 4 | Ex. 5 | Ex. 6 | Ex. 7 | Ex. 8 | Ex. 9 | Ex. 10 | Ex. 11 | Ex. 12 | Ex. 13 |
| --- | --- | --- | --- | --- | --- | --- | --- | --- | --- | --- | --- |
| External Phase | | | | | | | | | | | |
| Elastomer (DC9040) 12% active) | 55 | 62 | 62 | 40 | 41.5 | 25 | 31.5 | 21 | 17 | 17 | 50 |
| Dimethicone copolyol (Dow Corning 2-5185, 48% active in cyclomethicone) | 1 | 2 | 2 | 4 | 1 | 1 | 2.5 | 1 | 1 | 1 | 2 |
| Hydrogenated polyisobutene (Polyiso 250) | 5 | — | — | 8 | 5 | — | 5 | 1.5 | 1.5 | 1.5 | — |
| PPG-3 Myristyl Ether | 3 | 4.5 | 5 | — | 5 | 5 | — | 0.5 | 0.5 | 0.5 | 5.0 |
| C12-15 alkyl benzoate (FINSOLV TN) | — | — | — | 2 | — | — | — | — | — | — | — |
| Cyclomethicone (Dow Corning 245) | — | — | — | — | — | — | — | 5 | 9.0 | 9.0 | 2.0 |
| Fragrance | 1 | 1 | 1 | 1 | 1 | 1 | 1 | 1 | 1 | 1 | 1 |
| Internal Phase | | | | | | | | | | | |
| Antiperspirant Active[a] | 15 | 15.5 | 30 | 19.5 | 46.5 | 48.45 | 60.0 | 60.5 | 63.68 | 60.13 | 20 |
| Water (deionized)[b] | 20 | 15 | | 25 | | 19.55 | | 9.5 | 6.32 | 9.87 | 20 |
| Oleath-20 (HLB > 8) | — | — | — | 0.5 | — | — | — | — | — | — | — |
| Total | 100 | 100 | 100 | 100 | 100 | 100 | 100 | 100 | 100 | 100 | 100 |

[a]= See explanation of actives used.
[b]= Note that in the examples, sometimes the antiperspirant active is listed as a solution (which will include a water component) under the "active" designation with little or no water and sometimes the active and water are listed separately.

Examples 3–13

Compositions

The method described in Example 1 was used to make the compositions listed in Table A with the types and amounts of ingredients listed in the Table. Amounts are in percent by weight based on the total weight of the composition.

With regard to the active ingredients used, Westchlor Zr 35BX3 (77% solid actives on an anhydrous basis) dissolved in water was used for Examples 3, 4, 6 and 13. Westchlor Zr BX3 (33.55% actives on an anhydrous basis in water) was used for Example 7. An active as prepared by the method of Example 14 (41.28% solids on an anhydrous basis dissolved in water) was used for Examples 5 and 8. An active as prepared by the method of Example 14 (31.16% solids on an anhydrous basis dissolved in water) was used for Example 11. Summit AZG 368 (32% actives on an anhydrous basis dissolved in water) was used for Example 9. An active as prepared by Example 14 (33% actives on an anhydrous basis dissolved in water) was used for Examples 10 and 12.

cyclomethicone—elastomer described in U.S. Pat. No. 6,060,546). The Control Stick Example was Lady Speed Stick. The data shows that emulsion of the invention has conductivity as good as or better than the stick.

TABLE B

| Property | Ex. 3 | Ex. 4 | Ex. 5 | Ex. 6 | Ex. 7 | Ex. 8 | Ex. 9 | Ex. 10 | Ex. 11 | Ex. 12 | Ex. 13 |
|---|---|---|---|---|---|---|---|---|---|---|---|
| Initial Brookfield Viscosity (centipoise) | 240,000 | 170,000 | 310,000 | 185,000 | 132,000 | 205,000 | 280,000 | 320,000 | 225,000 | 260,000 | 270,000 |
| Brookfield Viscosity after 4 weeks at 49° C. (centipoise) | | | | | 140,000 | 210,000 | 278,000 | | | | 270,000 |
| Initial Carri-Med Complex Viscosity (Pascal seconds) | | 220 | | | 283 | 339 | 467 | | | | 206 |
| Carri-Med Complex Viscosity (Pascal seconds) after 4 weeks at 49° C. | | 213 | | | 274 | 319 | 515 | | | | 140 |

Examples 3–13

Viscosity

The viscosity of Examples 3–13 was evaluated using the method of Example 2 to obtain viscosity data from the Brookfield method and rheology data from the Carri-Med method. The data is shown in Table B.

Examples 3–13

Clarity

The clarity of Examples 3–13 was evaluated using visual observation. Compositions made according to Examples 3, 6, 7, 8, 9, 10, 11 and 12 gave clear products. Compositions made according to Examples 4 and 5 gave products that were not clear. A composition made according to Example 13 gave a translucent product.

Examples 3–13

Conductivity

The Standard Method described above was used with a 250 microliter drop of water placed on a 100 micron thick film of the test formula. Before the test each sample was equilibrated for 2 hours at 35 degrees C. and 85% relative humidity (simulation of underarm conditions). Since the Fixed Geometry Method was not used to obtain conductance data, for the listed Examples, the diameter of the spreading of the water drop is given. As noted above a minimum of 250 micro Siemens for the Fixed Geometry Method is the defined lower limit. Readings for conductivity using the Standard Method will be somewhat higher. The Control Gel Example was prepared using the same procedure as described for Examples 3–13 with 5% dimethicone copolyol (Dow Corning 2-5185 diluted to 40%); 1% Cyclomethicone (DC 245 (D5)); 53.37% antiperspirant active (28% in propylene glycol) (Westchlor 4105); 6.08% propylene glycol; 9.12% alcohol (SDA 40 200); 1.0% fragrance; 0.23% Tween 80; and 8.5% elastomer (5.8% actives in D5

The samples were prepared by matching the RI's of the two phases (within 0.005) and samples were visually observed to be clear.

Conductivity was evaluated for selected Examples using the Standard Method. The results are listed in TABLE C.

TABLE C

| Property | Ex. 3 | Ex. 5 | Ex. 7 | Ex. 8 | Ex. 9 | Ex. 11 | Ex. 12 | Ex. 13 |
|---|---|---|---|---|---|---|---|---|
| Conductivity at 100 seconds (micro Siemens) | 2182 | 851 | 701 | 4798 | 4216 | 5548 | 4403 | 3880 |
| Diameter of water droplet after spreading (cm) | 2.1 | 1.3 | — | 5.4 | 4.5 | 4.8 | 3.1 | 3.3 |
| Conductivity at 10 seconds (micro Siemens) | 1527 | 547 | 509 | 4511 | 3987 | 4842 | 3554 | 3412 |
| % oil phase | 65 | 70 | 53.5 | 32 | 40.0 | 30 | 30 | 60 |

The data in Table C may be compared with the data in Table D which is data for controls. Control stick #1 is Lady Speed Stick® antiperspirant (Mennen), and Control stick #2 is Right Guard® antiperspirant (Gillette). Normally a gel product does not have very good conductivity while stick products have much better conductivity. The data in Table C shows that compositions of the present invention have conductivity values comparable to stick products.

TABLE D

| Property | Control Gel #1 | Control Stick #1 | Control Gel #2 |
|---|---|---|---|
| Conductivity at 100 seconds (micro Siemens) | 180 | 3077 | |
| Diameter of water droplet after spreading (cm) | 0.87 | 1.7 | 1.2 |
| Conductivity at 10 seconds (micro Siemens) | 154 | 1627 | 295 ± 35 |
| % oil phase | 30 | (suspension) | 20 |

Examples 14–16

Experimental Antiperspirant Salts

Improved aluminum zirconium tetrachlorohydrex gly salt can be made using the following Examples 13–15. The goal is to enhance the smallest Al species (Peak-5) by lowering the metal:chloride molar ratio of the tetra-salt to be in the range of 1.2–0.9:1 and to stabilize the Zr polymeric species by raising the glycine/Zr molar ratio to be greater than 1.4:1.

Example 14

Glycine powder (159 g) is added to a zirconium compound (1000 g of a 31% solution of zirconium oxychloride ($ZrOCl_2$)) with stirring. Aluminum chlorohydrate ("ACH") (1120 g of a 50% aqueous ACH solution) is then added with additional stirring. The final solution is then diluted with distilled water into an anhydrous concentration of 33.0%, with a glycine/zirconium molar ratio of 1.45:1; aluminum/zirconium molar ratio of 3.56:1, and metal/chloride ratio of 1.01:1.

Example 15

Glycine powder (159 g) is added to a zirconium compound (1000 g of a 31% solution of zirconium oxychloride ($ZrOCl_2$) with stirring. ACH (1204 g of a 50% aqueous ACH solution) is then added with additional stirring. The final solution is then diluted with distilled water into an anhydrous concentration of 30.0% with a glycine/zirconium molar ratio as 1.45:1; an aluminum/zirconium molar ratio of 3.82:1, and a metal/chloride ratio of 0.98.

Example 16

A solution of $AlCl_3$ (200 g of 28% aqueous solution) is added to a ZAG solution (800 g of a 43% solution of Westchlor Zr 35BX3) with stirring. The mixture is then diluted into an anhydrous concentration of 30%. The final solution has an aluminum/zirconium molar ratio of 4.36:1; a metal/chloride ratio of 0.94:1; and a glycine/zirconium ratio of 0.97:1.

Analytical Data for Examples 14–16

Size exclusion chromatography ("SEC") or gel permeation chromatography ("GPC") are methods frequently used for obtaining information on polymer distribution in antiperspirant salt solutions. With appropriate chromatographic columns, at least five distinctive groups of polymer species can be detected in a ZAG, appearing in a chromatogram as peaks 1, 2, 3, 4 and a peak known as "5,6". Peak 1 is the larger Zr species (greater than 120–125 Å). Peaks 2 and 3 are larger aluminum species. Peak 4 is smaller aluminum species (aluminum oligomers) and has been correlated with enhanced efficacy for both ACH and ZAG salts. Peak 5,6 is the smallest aluminum species. The relative retention time ("Kd") for each of these peaks varies depending on the experimental conditions. Data for Table E was obtained by using the methods described in our patent U.S. Pat. No. 5,997,850, incorporated by reference herein as to the description of analytical techniques for obtaining peak analyses.

TABLE E

Polymer Distribution of the Improved Salts (SEC analysis)

| | Peak-1/Peak-3 | Peak-2/Peak-3 | Peak-4/Peak-3 | Peak-5/Peak-3 |
|---|---|---|---|---|
| Example 14 | 0 | 0.2 | 0.24 | 3.11 |
| Example 15 | 0 | 0.03 | 0.17 | 1.71 |
| Example 16 | 0.95 | 0.34 | 0.27 | 2.60 |
| WZR35BX3[a] | 0.55 | 0.24 | 0.18 | 0.55 | a = commercial salt from Westwood.

We claim:

1. A clear antiperspirant and/or deodorant composition in the form of an emulsion having a refractive index less than 1.42 and comprising:
   (a) 25–70% of an external phase comprising:
      (i) 0.1–10%, on an actives basis, of at least one elastomer which is a cyclomethicone (and) dimethicone crosspolymer made with an ≡Si—H containing polysiloxane and an alpha, omega-diene of formula $CH_2$=CH($CH_2$)$_x$CH=$CH_2$, where x=1–20, to form a gel by crosslinking and addition of ≡Si—H across double bonds in the alpha, omega diene, which crosspolymer has a viscosity in the range of 50,000–3,000,000 centipoise;
      (ii) 0.1–5% of a silicone copolyol having an HLB value ≦8;
      (iii) 0.1–68% of a volatile silicone selected in an amount to complete the external phase;
      (iv) 0–10% of a cosurfactant or emulsifier having an HLB value in the range of 1–15;
      (v) 0–5% of a non-volatile silicone; and
   (b) 30–75% of an internal phase which is made with:
      (i) 7–25% (on an anhydrous actives basis (excluding the waters of hydration) of an antiperspirant active;
      (ii) 0–10% ethanol;
      (iii) additional water as required to adjust the refractive index;
      (iv) 0–5% of an antimicrobial agent; and
      (v) 0–5% of an ionizable salt;
   wherein (1) the conductance of a water droplet applied to the surface of a thin film of the antiperspirant and/or deodorant composition is at least 250 micro Siemens/cm/ml as measured by a fixed geometry test at a loading of at least 7% by weight level of antiperspirant active; and (2) all amounts are in percent by weight based on the total weight of the composition.

2. A clear antiperspirant and/or deodorant composition according to claim 1 having an oil content of 25–50%.

3. A clear antiperspirant and/or deodorant composition according to claim 1 having an oil content of 30–45%.

4. A clear antiperspirant and/or deodorant composition according to claim 1 having an oil content of 40–70%.

5. A clear antiperspirant and/or deodorant composition according to claim 1 having an oil content of 30–60%.

6. A clear antiperspirant and/or deodorant composition according to claim 1 comprising 1–5% of the elastomer in cyclomethicone.

7. A clear antiperspirant and/or deodorant composition according to claim 1 comprising 0.1–1.0% of the silicone copolyol.

8. A clear antiperspirant and/or deodorant composition according to claim 1 wherein the silicone copolyol is one or more dimethicone copolyols.

9. A clear antiperspirant and/or deodorant composition according to claim 1 comprising 0–5% of the cosurfactant or emulsifier.

10. A clear antiperspirant and/or deodorant composition according to claim 1 wherein the cosurfactant or emulsifier is one or more members selected from the group consisting of:
   (a) sorbitan esters and ethoxylated sorbitan esters selected from the group consisting of PEG-20 sorbitan isostearate, sorbitan monolaurate, polysorbate-20, polysorbate-40, polysorbate-60, and polysorbate-80;
   (b) ethoxylates selected from the group consisting of Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10, and Oleath-20;
   (c) ethoxylated adducts selected from the group consisting of PEG-25 stearate, glyceryl stearate and PEG-100 stearate;

(d) PEG esters selected from the group consisting of PEG-8 oleate, PEG-8 laurate, PEG-8 dilaurate, PEG-12 dilaurate, PEG-80 diisostearate, and PEG-40 stearate;

(e) propoxylates selected from the group consisting of PPG-10 butanediol, PPG-50 oleyl ether, PPG-2-ceteareth-9, PPG-3-deceth-3, and PPG-5-ceteth-20;

(f) ethoxylated modified triglycerides selected from the group consisting of PEG-20 corn glycerides, and PEG-12 palm kernel glycerides;

(g) alkylphenol aromatic ethoxylates selected from the group consisting of dinonylphenol ethoxylate with 9 moles of ethylene oxide, octylphenol ethoxylate with 20 moles of ethylene oxide, octylphenol ethoxylate with 40 moles of ethylene oxide; and (h) block copolymers which are alkoxylated glycols having ethoxylated and propoxylated segments and which are selected from the group consisting of Poloxamer 182, Poloxamer 234, and Meroxapol 174.

11. A clear antiperspirant and/or deodorant composition according to claim 1 wherein the volatile silicone is added in an amount of 20–58%.

12. A clear antiperspirant and/or deodorant composition according to claim 1 wherein the volatile silicone is added in an amount of 20–50%.

13. A clear antiperspirant and/or deodorant composition according to claim 1 wherein the volatile silicone has a boiling point $\leq 250$ degrees C. at one atmosphere of pressure and is one or more members of the group consisting of (a) cyclic polydimethylsiloxanes represented by Formula III:

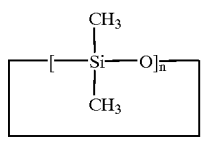

Formula III where n is an integer with a value of 3–7; and (b) linear polydimethylsiloxanes represented by Formula IV:

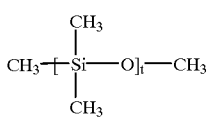

Formula IV and t is selected to obtain a viscosity of 1–200 centistokes.

14. A clear antiperspirant and/or deodorant composition according to claim 1 wherein the non-volatile silicone has a boiling point greater than 250 degrees at one atmosphere of pressure.

15. A clear antiperspirant and/or deodorant composition according to claim 1 wherein the non-volatile silicone is one or more members selected from the group consisting of phenyl trimethicone, dimethicone, phenylpropyltrimethicone, cetyl dimethicone, and dimethiconol.

16. A clear antiperspirant and/or deodorant composition according to claim 1 wherein the antiperspirant active is one or more members selected from the group consisting of aluminum salts, aluminum/zirconium salts, aluminum/zirconium salts complexed with a neutral amino acid.

17. A clear antiperspirant and/or deodorant composition according to claim 1 wherein the antiperspirant active is one or more members selected from the group consisting of aluminum chlorides, zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing.

18. A clear antiperspirant and/or deodorant composition according to claim 1 wherein the antiperspirant active is one or more members selected from the group consisting of aluminum chlorohydrate, aluminum chloride, aluminum sesquichlorohydrate, aluminum chlorohydrol-propylene glycol complex, zirconyl hydroxychloride, aluminum-zirconium glycine complex, aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, and aluminum zirconium tetrachlorohydrex gly dipropylene glycol complex.

19. A clear antiperspirant and/or deodorant composition according to claim 1 wherein the antiperspirant active is added to the composition in the form of a solution.

20. A clear antiperspirant and/or deodorant composition according to claim 1 wherein the antiperspirant active has a metal:chloride molar ratio in the range of 0.9–1.2:1 and a glycine:zirconium ratio greater than 1.4:1.

21. A clear antiperspirant and/or deodorant composition according to claim 20 wherein the antiperspirant active has a metal:chloride molar ratio in the range of 0.9–1.1:1.

22. A clear antiperspirant and/or deodorant composition according to claim 1 comprising an antimicrobial agent.

23. A clear antiperspirant and/or deodorant composition according to claim 1 comprising an ionizable salt of the form $M_a X_b$, where a=1 or 2; b=1 or 2; M is a member selected from the group consisting of $Na^{+1}$, $Li^{+1}$, $K^{+1}$, $Mg^{+2}$, $Ca^{+2}$, $Sr^{+2}$, $Sn^{+2}$, and $Zn^{+2}$, and X is a member selected from the group consisting of chloride, bromide, iodide, citrate, gluconate, lactate, glycinate, glutamate, ascorbate, aspartate, nitrate, phosphate, hydrogenphosphate, dihydrogenphosphate, formate, malonate, maleate, succinate, carbonate, bicarbonate, sulfate and hydrogensulfate.

24. A clear antiperspirant and/or deodorant composition according to claim 1 additionally comprising 0.5–50% of an emollient.

25. A clear antiperspirant and/or deodorant composition according to claim 24 wherein the emollient is selected from the group consisting of (a) fats and oils which are natural or synthetic glyceryl esters of fatty acids having a general structure of Formula VI:

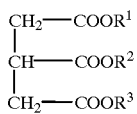

Formula VI wherein each of $R^1$, $R^2$, and $R^3$ may be the same or different and have a carbon chain length (saturated or unsaturated) of 7 to 30;

(b) hydrocarbons selected from the group consisting of paraffins, petrolatum, hydrogenated polyisobutene, and mineral oil, (c) esters of formula $R^4CO-OR^5$ wherein the chain length for $R^4$ and $R^5$ is independently selected to be in the range of from 7 to 30, $R^4$ and $R^5$ and can be saturated or unsaturated, straight chained or branched;

(d) saturated and unsaturated fatty acids having a formula $R^6COOH$ wherein $R^6$ has a carbon chain length from 7 to 30 and is straight chain or branched;

(e) saturated and unsaturated fatty alcohols having a formula $R^7COH$ where $R^7$ has a carbon chain length from 7 to 30 and is straight chain or branched;

(f) lanolin and its derivatives having a formula $R^8CH_2-(OCH_2CH_2)_nOH$ wherein $R^8$ represents the fatty groups derived from lanolin and n=5 to 75 or $R^9CO-(OCH_2-CH_2)_nOH$ where $R^9CO-$ represents the fatty acids derived from lanolin and n=5 to 100;

(g) alkoxylated alcohols wherein the alcohol portion is selected from aliphatic alcohols having 2–18 carbons, and the alkylene portion is selected from the group consisting of ethylene oxide, and propylene oxide having a number of alkylene oxide units from 2–53;

(h) ethers selected from the group consisting of dicaprylyl ether; dicetyl ether; dimethyl ether; distearyl ether; ethyl ether; isopropyl hydroxycetyl ether; methyl hexyl ether; polyvinyl methyl ether;

(i) silicones and silanes which are members of the group consisting of:
  (1) $(R^{10})_3SiO(Si(R^{11})_2O)_xSi(R^{12})_3$ where $R^{10}$, $R^{11}$ and $R^{12}$ can be the same or different and are each independently selected from the group consisting of phenyl and C1–C60 alkyl;
  (2) $HO(R^{14})_2SiO(Si(R^{15})_2O)_xSi(R^{16})_2OH$, where $R^{14}$, $R^{15}$ and $R^{16}$ and be the same or different and are each independently selected from the group consisting of phenyl and C1–C60 alkyl; or
  (3) organo substituted silicon compounds of formula $R^{17}Si(R^{18})OSiR^{19}$ which are not polymeric where $R^{17}$, $R^{18}$ and $R^{19}$ can be the same or different and are each independently selected from the group consisting of phenyl and C1–C60 alkyl optionally with one or both of the terminal R groups also containing an hydroxyl group;

(i) adipic acid blends selected from the group consisting of trimethyl pentanediol/adipic acid copolymer; trimethyl pentanediol/adipic acid/isononanoic acid copolymer; and adipic acid/diethylene glycol/glycerin crosspolymer; and (j) mixtures and blends of two or more of the foregoing.

26. A clear antiperspirant and/or deodorant composition according to claim 1 wherein the conductance is greater than 300 micro Siemens/cm/ml.

27. A clear antiperspirant and/or deodorant composition according to claim 1 wherein the conductance is greater than 400 micro Siemens/cm/ml.

28. A clear antiperspirant and/or deodorant composition according to claim 1 wherein the conductance is greater than 500 micro Siemens/cm/ml.

29. A clear antiperspirant and/or deodorant composition according to claim 1 wherein the elastomer has a viscosity in the range of 100,000–1,000,000 centipoise.

30. A clear antiperspirant and/or deodorant composition according to claim 1 wherein the elastomer has a viscosity in the range of 250,000–450,000 centipoise.

* * * * *